United States Patent [19]
Planas et al.

[11] Patent Number: 6,130,075
[45] Date of Patent: Oct. 10, 2000

[54] POLYMER CONJUGATES OF POLYETHYLENE GLYCOLS OR OXIDES WITH POLYETHYLENEIMINE OR POLYPROPYLENIMINE FOR EXTRACTING CARBOXYLIC ACIDS FROM SOLUTIONS

[75] Inventors: Jordi Planas; Folke Tjerneld; Bärbel Hahn-Hägerdal, all of Lund, Sweden

[73] Assignee: Forskarpatent I Syd AB, Lund, Sweden

[21] Appl. No.: 09/296,255

[22] Filed: Apr. 22, 1999

Related U.S. Application Data

[60] Provisional application No. 60/082,609, Apr. 22, 1998.
[51] Int. Cl.$^7$ ............................... C12P 7/00; C12P 7/40; C12P 7/48; C12P 7/56
[52] U.S. Cl. ..................... 435/139; 435/144; 435/136; 435/132
[58] Field of Search ................................. 435/139, 136, 435/144, 132

[56] References Cited

FOREIGN PATENT DOCUMENTS

| | | |
|---|---|---|
| 0 364 208 A1 | 4/1990 | European Pat. Off. . |
| 0 541 018 A2 | 5/1993 | European Pat. Off. . |
| 39 01 281 A1 | 7/1990 | Germany . |
| 197 26 186 A1 | 12/1998 | Germany . |
| 92/07006 | 4/1992 | WIPO . |
| 92/07023 | 4/1992 | WIPO . |
| 98/59064 | 12/1998 | WIPO . |

OTHER PUBLICATIONS

Alred et al., "Application of temperature-induced phase partitioning at ambient temperature for enzyme purification," *J. Chromatogr.*, 1994, 659:289–298.

Alred et al. "Synthesis of dye conjugates of ethylene oxide–propylene oxide copolymers and application in temperatue–induced phase partitioning," *Bioseparation*, 1992, 2:363–373.

Dissing et al., "Poly(ethyleneimine) as a phase-forming in aqueous two–phase systems," *Biotechnol. Appl. Biochem.*, 1993, 17:15–21.

King, "Amine-based systems for carboxylic acid recovery," *Chemtech*, May 1992, pp. 285–291.

Kwon et al., "Extractive Lactic Acid Fermentation in Poly-(ethyleneimine)–Based Aqueous Two-Phase System," *Biotechnol. Bioeng.*, May 5, 1996, 50:280–290.

Larsson et al., "Characterization of Aqueous Two-Phase Systems Based on Polydisperse Phase Forming Polymers: Enzymatic Hydrolysis of Starch in a PEG–Starch Aqueous Two–Phase System," *Biotechnol. Bioeng.*, 1998, 31:979–983.

Planas et al., "Amine-based aqueous polymers for the simultaneous titration and extraction lactic acid in aqueous two-phase systems," *J. Chromatogr. B.*, 1988, 711:265–275.

Tamada et al., "Extraction of Carboxylic Acids with Amine Extractants. 1. Equilibria and Law of Mass Action Modeling," *Ind. Eng. Chem. Res.*, 1990, 29:1319–1326.

Tamada et al., "Extraction of Carboxylic Acids with Amine Extractants. 2. Chemical Interactions and Interpretation of Data," *Ing. Eng. Chem. Res.*, 1990, 29:1327–1333.

Tamada et al., "Extraction of Carboxylic Acids with Amine Extrantants. 3. Effect of Temperature, Water Coextraction, and Process Consideration," *Ind. Eng. Chem. Res.*, 1990, 29:1333–1338.

Vanancio et al., "Evaluation of Crude Hydroxypropyl Starch As a Bioseparation Aqueous–Phase–Forming Polymer," *Biotechnol. Prog.*, 1993, 9:635–639.

*Primary Examiner*—Francisco Prats
*Assistant Examiner*—Susan D. Coe
*Attorney, Agent, or Firm*—Finnegan, Henderson, Farabow, Garrett & Dunner, L.L.P.

[57] ABSTRACT

The invention provides novel polymer conjugates that are especially useful in the separation of carboxylic acids from complex fermentation compositions. The polymer conjugates comprise polyethylene glycols or oxides and polyethyleneimine or polypropyleneimine in various ratios. The novel polymer conjugates permit enhanced extraction of carboxylic acids from fermentation systems not only through their use in partitioning the carboxylic acids from various polymeric components of the fermentation system, but also through their use in adjusting the pH of the system for optimal performance and separation.

7 Claims, 1 Drawing Sheet

POLYMER CONJUGATES OF POLYETHYLENE GLYCOLS OR OXIDES WITH POLYETHYLENEIMINE OR POLYPROPYLENIMINE FOR EXTRACTING CARBOXYLIC ACIDS FROM SOLUTIONS

CROSS-REFERENCE TO RELATED APPLICATION

This application is based on, and claims benefit of, United States Provisional Application No. 60/082,609, filed Apr. 22, 1998. The entire disclosure of the Provisional Application is relied upon and incorporated by reference herein.

BACKGROUND OF THE INVENTION

1. Field of the Invention

This invention relates to the extraction of carboxylic acids from solutions containing them. More particularly, this invention relates to polymer conjugates of polyethylene glycols or oxides with polyethyleneimine or polypropylenimine for use in such extraction processes, and the extraction processes.

2. Description of Related Art

Carboxylic acids are promising intermediates in a bioprocessing complex, because the oxygen of the biomass is placed in a form that is useful for further reaction with many other products. Lactic, propanoic (propionic), succinic, and citric acids among others fall in this group, and are, or have been, manufactured via fermentation.

Lactic acid has been produced via fermentation since 1881, and in 1990 about 20,000 tons/year were obtained fermentatively, accounting for half of the lactic acid world production, the remainder of the lactic acid being produced in chemical processes. The main destinations of lactic acid are food and pharmaceutical industries, but an emerging polymer industry is increasing the demand for the production of lactic acid to be used as monomers in the synthesis of thermostable and biodegradable plastics.

The main drawback in the fermentative production of carboxylic acids is that, during their production, an accumulation of the acid in the medium results in inhibition of cell growth as well as production of the acid itself. Continuous high productivity bioreactors with cell recirculation systems facilitating cell separation and resulting in high cell densities may be used to improve the performance of fermentation-based processes and thus make them economically more attractive. Drawbacks, such as limited diffusion of the nutrients and release of cells, have been reported in systems with cells entrapped within porous matrices or by microencapsulation. Centrifugation and filtration are useful systems for cell separation, but result in high stress levels that decrease the performance of the fermentation process when used as cell recirculation systems.

These disadvantages are avoided when cells are entrapped in a two-phase emulsion obtained by mixing a water solution with a suitable organic solvent, such that the cells grow in the aqueous phase and the product can be removed from the organic phase. However, organic solvents are often injurious and even toxic to the cells.

The use of a two-phase system based on aqueous solutions of two polymers, as an extractive fermentation system, provides a more biocompatible environment for the cells than aqueous-organic two-phase systems. The uneven partitioning of cells in aqueous two-phase systems (ATPSs) allows the implementation of a stress free cell recycling process.

From economical considerations the use of cheap raw material for the production of lactic acid must be considered. Starchy material, such as potato starch, tapioca starch, wheat starch, or, more suitably, corn starch, can be hydrolyzed and used as a substrate for the fermentation. A further advantage is that starch might be used as phase-forming polymer. Thus, having a double function as feed stock and phase forming polymer, the use of starch makes the process certainly much more interesting from an economic point of view.

Recovery of lactic acid is impeded by the complex nature of fermentation broths, by dilute product streams, and by the physico-chemical properties of lactic acid itself, which can not be distilled and which is difficult to crystallize. At present, the most widely used process for the recovery of lactic acid involves precipitation and filtration of the calcium salt of the acid. Treatment of the precipitate with sulphuric acid leads to preferential precipitation of $CaSO_4$, which is filtered off. Concentration by water, evaporation, and purification by crystallization are used to achieve the final product specifications. This method has the disadvantage of irreversibly consuming the base used for the titration of lactic acid during the fermentation and the sulphuric acid, leaving as waste large quantities of sulphate, which gives rise to disposal problems.

Alternative techniques, such as extraction and sorption, have been developed. Extraction of lactic acid can be performed by three different extractant categories: (i) Carbon-bonded, oxygen-bearing extractants; (ii) phosphorous-bonded, oxygen-bearing extractants; and (iii) high molecular weight aliphatic imines. The first two categories are based on the solvation of the acid by the donor bonds resulting in weak and nonspecific interactions between the acid and the solvent. Thus, they are not recommended for lactic acid extraction. In the third category, a specific reaction of proton transfer between the lactic acid and the imine occurs. This allows a further ion-pair interaction between the acid and the imine, bringing the lactic acid to the organic phase.

In extractive fermentation, these systems have a main drawback because of their toxic effect on organisms. Therefore, immobilization of the amine based compounds in solid sorbents has been used in lactic acid production. The low capacity of the resins, typically between 0.1–0.2 g lactic acid/g resin, and the fact that they are solid and must be continuously added to the fermentor as lactic acid is being synthesized, makes these processes difficult to operate.

Polyethyleneimine (PEI), has been used as a phase-forming polymer in ATPS. Ethylene oxide-propylene oxide random copolymers (EOPO) are phase-forming polymers when mixed with starch and are easily recyclable by temperature-induced phase separation and, thus, of great technical interest. As a drawback, both cells and carboxylic acids tend to partition to the starch rich phase of EOPO-Dextran (DEX) ATPS making the carboxylic acid recovery process inefficient.

Accordingly, there exists a need in the art for improved methods for recovering carboxylic acids, such as lactic acid, from solutions, particularly fermentation mixtures containing the acids. In addition, there exists a need in the art for reagents for facilitating the removal of carboxylic acids from such solutions.

SUMMARY OF THE INVENTION

This invention aids in fulfilling these needs in the art by providing a new family of polymer conjugates obtained by covalently linking any type of polyethylene glycol (PEG), ethylene oxide (EO)—propylene oxide (PO) random copolymer (at any molar ratio of ethylene oxide/propylene oxide), or propylene oxide (PO), with any type of polyethyleneimine (PEI) or polypropylenimine (PPI). Being low molecular weight polymers, they are more effective for the purpose of extracting carboxylic acids from solutions that contain such acids. The low molecular weight polymers are especially useful for extracting carboxylic acids from fermentation systems based on the fermentation of polysaccharides such as dextran, starch, or mixtures thereof.

BRIEF DESCRIPTION OF THE DRAWING

This invention will be described in greater detail with reference to the drawing in which.

DETAILED DESCRIPTION OF PREFERRED EMBODIMENTS

Figure 1:
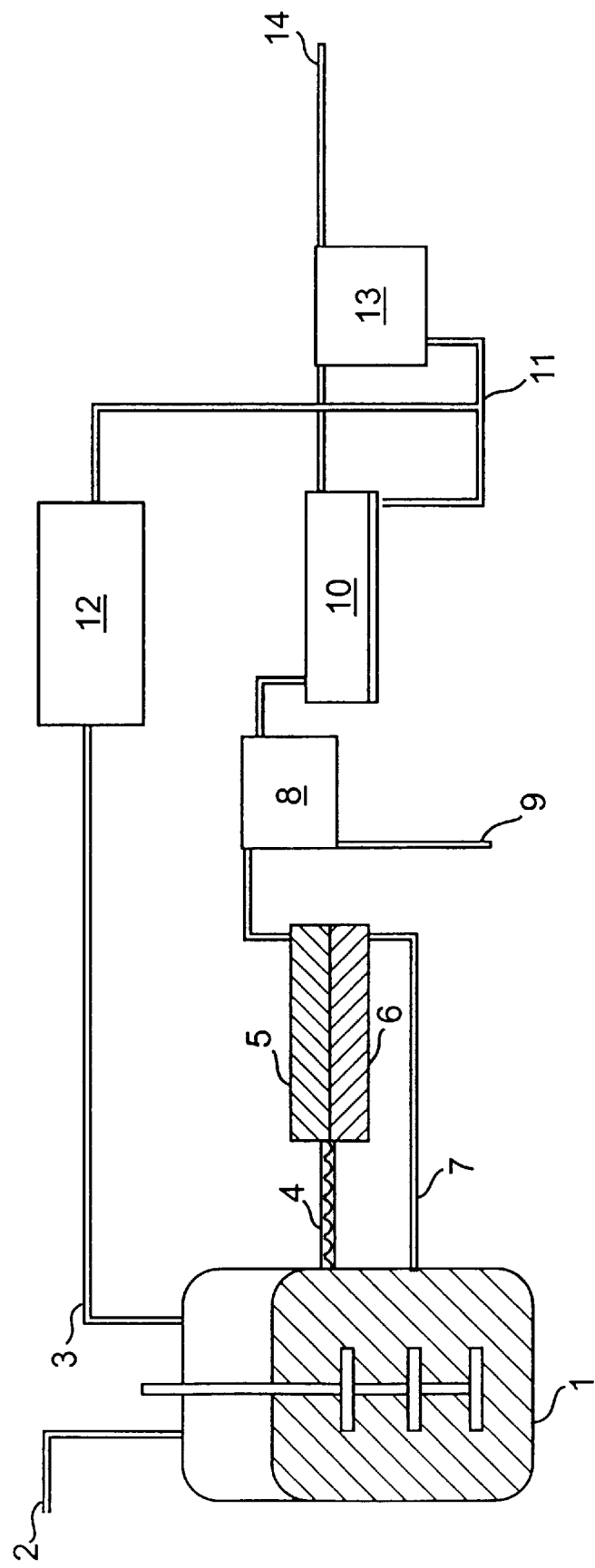
FIG. 1 is a flow sheet for the extraction of carboxylic acids from a fermentation medium.

In a first aspect of the invention, conjugate polymers are provided. The conjugate polymers can be used for multiple application, including, but not limited to, extraction of carboxylic acids from fermentation compositions and as pH modifiers for various organic and inorganic processes and compositions.

In embodiments of this aspect of the invention, polymers, copolymers, terpolymers, and higher order polymers are provided as conjugates of various polymers linked together through covalent bonds. For example, copolymers of propylene oxide and polyethyleneimine; polyethylene glycol and polyethyleneimine; propylene oxide and polypropylenimine; and polyethylene glycol and polypropylenimine are provided. In addition, a random copolymer of ethylene oxide and propylene oxide can be conjugated with polyethyleneimine or with polypropylenimine.

The polymers can be incorporated into the conjugates of the invention in any relative proportions. For example, a conjugate polymer can be formed from propylene oxide and polyethyleneimine where the starting compounds are combined in a molar ratio of from 100:1 to 1:100. Preferably, the starting compounds are added at a ratio of approximately 10:1 to 1:10. More preferably, the compounds are added at a ratio of approximately 8:1 to 1:1.

The new conjugate polymers of this invention make it possible to implement a process for extractive fermentation in carboxylic acid production. In an embodiment of the invention, a process for extracting carboxylic acids from a fermentation system is provided in which the process comprises:

(a) providing a composition comprising carboxylic acid fermentation products;

(b) adding the polymer conjugate of claim 1 to form a mixture;

(c) separating the mixture into two phases, a heavy phase and a light phase, wherein the light phase comprises at least one carboxylic acid fermentation product;

(d) optionally further separating the light phase into two phases, a phase containing said polymer conjugate and other polymers, and a phase containing said at least one carboxylic acid fermentation product.

The process can be a continuous process, which further comprises reusing the conjugate and polymer-containing phase from step (d) as the polymer conjugate in step (b).

In preferred embodiments, the fermentation system is a system in which polysaccharides are fermented.

A preferred embodiment of the invention is depicted in the Figure. A reactor (1), in which an extractive fermentation in ATPS is taking place in a continuous mode, has an inlet (2) for a carbohydrate feed (fermentable sugars in water and/or carbohydrate polymer in water). An EOPO-PEI conjugate is added via inlet (3) at a rate determined by its basicity and is controlled by a control unit coupled to a pH meter so that the pH in the reactor is maintained at the desired values. The reactor has an outlet (4) from which the fermentation broth, containing mainly the two-phase forming polymers, the biomass, and the carboxylic acid product, is continuously removed at a rate defined by the specific operational conditions that are chosen.

The outgoing fermentation broth is pumped to a liquid-liquid separation device (5). The separation device (5) can be a settler, a liquid-liquid centrifuge, or any other suitable device. A heavy phase stream (6) is obtained in the liquid-liquid separation process, which contains mainly a carbohydrate-rich phase. This stream is pumped back to the fermentor (7), thus achieving a certain degree of biomass recirculation, the degree being determined by the recirculation flow-rate, the partition coefficient of the microorganism in the phase system, and the characteristics and operational conditions of the liquid-liquid separation device.

From the liquid-liquid separation device (5), a light phase is obtained containing mainly a conjugate, polymer-rich phase depleted in biomass and enriched in the product carboxylic acid. The light phase obtained after the liquid-liquid separation process can be further processed in separation chamber (8) to eliminate any trace of biomass. Any well-known method for solid-liquid separation can be used.

Two main objectives are achieved in the separation in separation chamber (8): (i) A cell free product stream is obtained for further processing; and (ii) the necessary biomass bleeding of the system is performed at element (9). The cell free product stream containing the conjugate polymer is pumped to a liquid-liquid separation device (10), which can be run at a temperature that will be optimized for each type of product stream, and in any case, will be above the cloud point of this product-polymer stream.

Two phases are obtained during this process, a heavy phase and a light phase. The heavy phase is a conjugate, polymer-rich phase containing the conjugate polymer at high concentration, minor amounts of water, and carboxylic acid product. This heavy phase can be pumped via a pump (11) to a regenerator (12) where regeneration is performed. Regeneration allows the heavy phase to be reused in the reactor as titrating base and phase forming polymer.

The light phase obtained in the liquid-liquid separation device (10) containing mainly water, the carboxylic acid product, and a small amount of the conjugate polymer can be submitted to a process to separate the residual conjugate polymer in separator (13). This separation of the residual polymer conjugate might be obtained by ultrafiltration, electrodialysis, or any other suitable method. Thus, a concentrated polymer solution is pumped to the recirculating conjugate polymer-rich stream via pump (11), and a polymer free carboxylic acid product stream (14) is obtained and can be further processed to obtain the final carboxylic acid product.

The new family of polymer conjugates can be considered multi-use polymers for the purpose of the present invention. First of all, due to their basic character (typically pH above 10), they can be used as titrating bases for the fermentative production of carboxylic acids, thus avoiding the use of the inorganic bases commonly used in these processes in order to control the pH. Secondly, since the new conjugates show polymer-polymer incompatibility when mixed with polysaccharide polymers, such as dextran or starch, aqueous two-phase systems are formed providing a suitable and stress free system for the production of carboxylic acids where biomass partitions mainly to the polysaccharide-rich phase, and the carboxylic acid partitions mainly to the conjugate-rich phase. This provides a method for the removal of the inhibitory carboxylic acid from the fermentation broth. Third, the recycling of the conjugate might be easily performed by temperature-induced precipitation since the conjugate shows this precipitation behavior typically below 100° C., which can be enhanced by the addition of phosphate salt to the conjugate-rich phase.

This invention will be more fully understood by reference to the following Examples.

EXAMPLES

Chemicals

Polymer stock solutions were prepared in ultra-pure water (Milli-RO4 water purification system, Millipore, Bedford, Mass., U.S.A.). $EO_{50}PO_{50}$ (50% ethylene oxide; 50% propylene oxide random copolymer, $M_r$~3,900) was from International Speciality Chemicals (Southampton, U.K.), and dextran T 500 (DEX) was from Pharmacia Biotech Norden (Sollentuna, Sweden) DL-lactic acid (2-hydroxy propanoic acid) 85% in water was obtained from Acros Organics (New Jersey, N.J., U.S.A.). Propionic acid for synthesis grade, and citric acid monohydrate (GR) were obtained from Merck (Darmstadt, Germany). Succinic acid was obtained from Sigma (Sigma Chemical Company, St. Louis, Mo., U.S.A.). NaOH pellets (GR) from Merck were used to adjust the pH of the acid stock solutions, m-phosphoric acid (pro analysis grade), sodium dihydrogen phosphate (extra pure grade), and disodium hydrogen phosphate (extra pure grade), from Merck were used to prepare phosphate stock solutions at different pH.

Polymer Conjugates

Four different polymer conjugates were provided by A. Kozlowski from the department of Material Sciences in the University of Alabama at Tuscalosa (Ala., U.S.A.). Two PEG-PEI conjugates based on PEG (5 K) and PEI (10 K) were synthesized. By reacting different proportions of the two polymers a PEG-PEI (2:1) conjugate with a 4:1 molar ratio (2:1 weight ratio) and a PEG-PEI (4:1) conjugate with a 8:1 molar ratio (4:1 weight ratio) were obtained. Using PO (UCON-LB-135, average molecular weight 4000, Union Carbide, New York, U.S.A.) and PEI (600), a PO-PEI conjugate with a molar ratio of 1.58:1.00 was obtained. Using $EO_{50}PO_{50}$ (50% EO, 50% PO random copolymer, UCON 50HB5100, average molecular weight 4000, Union Carbide, New York, U.S.A.) and PEI (600), a EOPO-PEI (weight ratio 8:1) conjugate with a molar ratio of 1.20:1.00 was obtained.

Partitioning Studies

The partitioning of the carboxylic acids and BSA was determined in different ATPS. The control $EO_{50}PO_{50}$-DEX phase systems were made up by mixing appropriate amounts of polymer stock solutions with carboxylic acids or BSA stock solutions, which had been previously pH adjusted (PHM82 standard pH meter, Radiometer, Copenhagen, Denmark), with phosphate stock solutions, and adding distilled water to 3.0 g. Partitioning in the conjugate-DEX systems was performed by mixing the appropriate amounts of DEX stock solution and conjugate/carboxylic acid stock solution. Conjugate/carboxylic acid stock solutions were obtained by titrating the conjugate with the carboxylic acid to the desired pH, and after adding, where necessary, the appropriate amount of phosphate stock solution, distilled water was added to a final weight or 3.0 g. The tubes were capped and gently shaken for 30 min. The phase separation was allowed to occur for 5 h at 30° C. Each phase system was made in duplicate, samples from the top and bottom phases were removed and further analyzed for carboxylic acid or BSA concentration, and for phase forming polymer concentration when possible.

Analysis

Analysis of carboxylic acids and of phase composition in the case of EOPO-PEI-DEX systems, was performed by HPLC using a prepacked gel exclusion chromatography column (Ultrahydrogel 500, 300×7.8 mm I.D.; Waters, Millipore Corporation, Milford, Mass. U.S.A.) at 22° C. Eluent flow was provided by a LC pump (LC 6A model, Shimazu Corporation, Kyoto, Japan). Samples were injected in the flow line by an autosampler (Marathon model, Spark Holland, Emmen, the Netherlands).

BSA concentration was determined by measuring absorbence at 280 nm (V-2000 spectrophotometer, Hitachi Ltd, Tokyo, Japan) using a top or a bottom phase of a phase system without BSA as blank for the samples from the top and bottom phases of the phase systems containing BSA. The BSA standard curve was obtained from by diluting a 2 mg/ml stock solution (Albumin Standard, Pierce, Rockford, Ill. U.S.A.)

Lactic Acid Partitioning in PEG-PEI Based ATPS

The partitioning of lactic acid was investigated in PEG-PEI(2:1)-DEX and PEG.PEI(4:1)-DEX ATPS. The influence of the presence in the ATPS of 2% (w/w) of Na-phosphate was investigated at different pH for systems containing 10.0% PEG.PEI(2:1)-8% DEX. The specific conditions used as well as the results in terms of volume ratio of the resulting ATPS, and lactic acid partition coefficient are summarized in Table 1.

TABLE 1

Partitioning of lactic acid in ATPS containing 10.0% of PEG(5K)-PEI(10K) conjugate (molar ratio 4:1, weight ratio 2:1) and 8.0% DEX (500K) at 30° C.

| pH | 2% Na-Phosphate | [lactic acid] | (%) Vol. ratio | $K_{lac}$ | $\delta_{n-1}$ |
|---|---|---|---|---|---|
| 6.4 | + | 4.3 | 1.7 | 1.22 | 0.01 |
|  | − | 4.3 | 0.6 | 0.9 | 0.1 |
| 4.9 | + | 5.2 | 2 | 1.54 | 0.01 |
|  | − | 5.2 | 0.7 | 0.99 | 0.09 |
| 4.3 | + | 5.9 | 2 | 1.66 | 0.08 |
|  | − | 5.9 | 0.6 | 1.00 | 0.02 |

The influence of the presence of 2% (w/w) Na-phosphate, the influence of temperature, and the influence of polymer concentration on $K_{lac}$ were investigated in PEG.PEI(4:1)-DEX ATPS. The specific conditions used as well as the results in terms of volume ratio of the resulting ATPS, and lactic acid partition coefficient are summarized in Table 2. Since the composition of the resulting phases could not be analyzed with the method described in the Material and Methods section, the phase volume ratio was used as an indicator of the influence of the different factors on the phase systems.

TABLE 2

Partitioning of lactic acid in ATPS containing PEG(5K)-PEI(10K) conjugate (molar ratio 8:1, weight ratio 4:1) and DEX (500K) at pH 6.0

| ATPS composition | T (° C.) | 2% Na-Phosphate | [lactic acid] | Vol. (% ratio) | $K_{lac}$ | $\delta_{n-1}$ |
|---|---|---|---|---|---|---|
| 10.0% PEG-PEI-8.0% DEX | 30 | – | 2.7 | 1.3 | 1.40 | 0.03 |
| 10.0% PEG-PEI-8.0% DEX | 30 | + | 2.7 | 2.4 | 1.59 | 0.03 |
| 10.0% PEG-PEI-8.0% DEX | 40 | + | 2.7 | 2.4 | 1.63 | 0.01 |
| 12.0% PEG-PEI-10.0% DEX | 30 | + | 3.0 | 2.4 | 1.75 | 0.09 |
| 12.0% PEG-PEI-10.0% DEX | 40 | + | 3.0 | 2.4 | 1.73 | 0.02 |

Partitioning of Carboxylic Acids in ATPS

In order to evaluate the performance of the new conjugates for their organic acid extractive capacity, the partitioning of lactic, propanoic, and succinic acids ($K_{AH}$) was determined in neutral ATPC containing 10% $EO_{50}PO_{50}$-8% DEX and 2% of Na-phosphate. These results were considered as control values to be compared with $K_{AH}$ values obtained when lactic, propanoic, succinic, and citric acids were partitioned in 10% $EO_{50}PO_{50}$.PEI-8% DEX. The specific conditions used as well as the results in terms of volume ratio of the resulting ATPS, and lactic acid partition coefficient are summarized in Table 3. Table 3: Partitioning of carboxylic acids in ATPS containing 2% Na-phosphate, at pH 6.0 and 30° C. The cloud point[1] values were obtained by warming up the resulting top phases of the respective phase systems.

| ATPS composition | [total acid] | Cp (° C.) | $K_{lac}$ | $\delta_{n-1}$ |
|---|---|---|---|---|
| 10% $EO_{50}PO_{50}$-8% DEX | 3.0% lactic | ~39 | 0.88 | 0.03 |
| 10% $EO_{50}PO_{50}$-8% DEX | 3.0% propanoic | 40 | 0.87 | 0.02 |
| 10% $EO_{50}PO_{50}$-8% DEX | 3.0% succinic | ~32 | 0.25 | 0.02 |
| 10% $EO_{50}PO_{50}$-PEI-8% DEX | 1.7% lactic | * | 2.1 | 0.1 |
| 10% $EO_{50}PO_{50}$-PEI-8% DEX | 1.0% propanoic | ~73 | 1.12 | 0.3 |
| 10% $EO_{50}PO_{50}$-PEI-8% DEX | 0.9% succinic | ~73 | 1.15 | 0.4 |
| 10% $EO_{50}PO_{50}$-PEI-8% DEX | 0.8% citric | ~65 | 1.30 | 0.2 |

[1]The cloud point is the temperature value at which precipitation of a polymer in water solution occurs.
*No clouding was observed even at 110° C.

Thermal Precipitation Characteristics of the $EO_{50}PO_{50}$.PEI Conjugate

The cloud point (Cp) of the top phases of the 10% $EO_{50}PO_{50}$-8% DEX ATPS containing respectively lactic, propanoic, and succinic acids was determined. These results were considered as control values to be compared with Cp values obtained for the top phases of 10% $EO_{50}PO50$-8% DEX ATPS containing lactic, propanoic, succinic, and citric acids, respectively.

What is claimed is:

1. A process for extracting carboxylic acids from a fermentation system, wherein said process comprises:

(a) providing a composition comprising carboxylic acid fermentation products;

(b) adding the polymer conjugate comprising:
        (i) a polymer selected from the group consisting of polyethylene glycol, ethylene oxide/propylene oxide random copolymer, and propylene oxide, and
        (ii) polyethyleneimine or polypropylenimine,
    wherein (i) and (ii) are covalently linked to form said polymer conjugate, and wherein adding (b) to (a) forms a mixture;

(c) separating the mixture into two phases, a heavy phase and a light phase, wherein the light phase comprises at least one carboxylic acid fermentation product; and (d) optionally further separating the light phase into two phases, a phase containing said polymer conjugate and other polymers, and a phase containing said at least one carboxylic acid fermentation product.

2. The process of claim 1, wherein the process is a continuous process, which further comprises reusing the conjugate and polymer-containing phase from step (d) as the polymer conjugate in step (b).

3. The process of claim 1, wherein the process is an extractive fermentation in an aqueous-organic two-phase system.

4. The process of claim 1, wherein the fermentation system is a system in which polysaccharides are fermented.

5. The process of claim 4, wherein the polysaccharides are selected from the group consisting of dextran, starch, a sugar, and a combination of dextran, starch, and/or a sugar.

6. The process of claim 1, wherein the process is a continuous process and wherein the heavy phase obtained in step (c) is added to the mixture of step (b).

7. The process of claim 1, wherein at least a portion of step (d) is performed above the cloud point of the light phase.

* * * * *